(12) United States Patent
Damarati

(10) Patent No.: US 7,794,409 B2
(45) Date of Patent: Sep. 14, 2010

(54) MULTIPLE BIOPSY DEVICE

(75) Inventor: John Jairo Damarati, Tokyo (JP)

(73) Assignee: Boston Scientific Scimed, Inc., Maple Grove, MN (US)

( * ) Notice: Subject to any disclaimer, the term of this patent is extended or adjusted under 35 U.S.C. 154(b) by 714 days.

(21) Appl. No.: 11/036,927

(22) Filed: Jan. 14, 2005

(65) Prior Publication Data

US 2005/0124913 A1    Jun. 9, 2005

Related U.S. Application Data

(63) Continuation of application No. 10/118,202, filed on Apr. 5, 2002, now Pat. No. 6,858,014.

(51) Int. Cl.
*A61B 10/00*    (2006.01)

(52) U.S. Cl. ................ 600/565; 600/564; 600/127; 600/129

(58) Field of Classification Search ......... 600/104–107, 600/121, 123, 127, 129, 562, 564–568; 604/22; 606/167, 170, 171

See application file for complete search history.

(56) References Cited

U.S. PATENT DOCUMENTS

| | | | |
|---|---|---|---|
| 5,100,426 A * | 3/1992 | Nixon | ................ 606/170 |
| 5,106,364 A | 4/1992 | Hayafuji et al. | |
| 5,409,012 A | 4/1995 | Sahatjian | |
| 6,142,956 A | 11/2000 | Kortenbach et al. | |
| 7,081,097 B2 * | 7/2006 | Martone et al. | ............. 600/562 |

FOREIGN PATENT DOCUMENTS

| | | |
|---|---|---|
| WO | WO 97/24070 A1 | 7/1997 |
| WO | WO 00/44285 A1 | 8/2000 |

* cited by examiner

*Primary Examiner*—Max Hindenburg
*Assistant Examiner*—Jonathan M Foreman
(74) *Attorney, Agent, or Firm*—Finnegan, Henderson, Farabow, Garrett & Dunner LLP

(57) ABSTRACT

A multiple biopsy device has a number of chambers into which tissue samples are received. A cutting mechanism, such as a blade, moves relative to the chambers to cut a tissue sample that is within a chamber. In one embodiment of the invention, the multiple biopsy device is removably secured to the distal end of an endoscope/bronchoscope.

26 Claims, 2 Drawing Sheets

MULTIPLE BIOPSY DEVICE

CROSS-REFERENCE TO RELATED APPLICATION

The present application is a continuation of U.S. patent application Ser. No. 10/118,202, filed Apr. 5, 2002, now U.S. Pat. No. 6,858,014 the benefit of which is claimed under 35 U.S.C. §120 and which is herein incorporated by reference.

FIELD OF THE INVENTION

The present invention relates to medical devices and in particular to devices for obtaining biopsy samples from interior body cavities.

BACKGROUND OF THE INVENTION

In addition to obtaining a visual inspection with an endoscope/bronchoscope, etc., many physicians will biopsy a region of interest in order to confirm or deny the presence of disease.

The conventional method of obtaining a tissue sample is with a biopsy forceps. Most forceps have an elongated shaft that terminates at a sharp cutter with a tissue receptacle at the distal end. The forceps are threaded through a biopsy channel of the endoscope and a tissue sample is obtained. The forceps are then withdrawn from the endoscope and an assistant picks out the sample with a tweezers and places it in a numbered collection device so that the location of the tissue sample can be traced. The forceps are then reinserted in the endoscope to collect another sample at another collection point. This process is not only time consuming but adds wear and tear on the endoscope caused by the repeated insertion and withdrawal of the forceps.

There exist some biopsy forceps that hold multiple tissue samples in a single receptacle. However, they are not commonly used because the samples may commingle resulting in a loss of traceability. In addition, there is some chance that the samples may cross contaminate each other.

Given these problems there is a need for a multiple biopsy device that can easily obtain multiple tissue samples without requiring the device to be repeatedly withdrawn and inserted into the patient and will not commingle or cross contaminate the tissue samples.

SUMMARY OF THE INVENTION

A device for obtaining multiple biopsy samples from a patient has a cap positioned at the distal end of an endoscope. The cap has two or more chambers in which tissue samples are received. A cutter cuts tissue that has entered a chamber. The chamber is then sealed and another chamber is positioned to receive another tissue sample.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
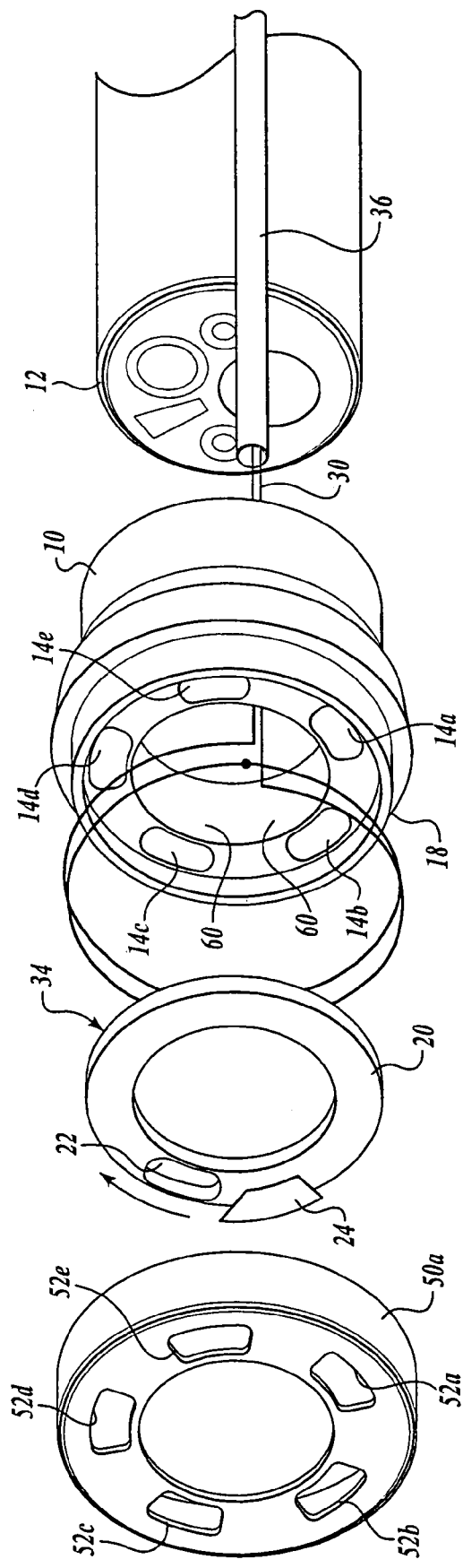
FIG. 1 is an exploded view of one embodiment of a multiple biopsy device according to the present invention.

In accordance with one embodiment of the present invention, a multiple biopsy device 10 comprises a cap that is fitted over the distal end of a conventional endoscope/bronchoscope 12 or other type of device that lets a physician visually examine internal body cavities. The biopsy device 10 has a lumen passing through the center with two different radiuses. At the proximal end, the lumen is sized such that it will snugly fit over the outer diameter of the endoscope. The lumen has a second, narrower, diameter toward the distal end that forms a step that engages the end of the endoscope such that the biopsy device cannot slide along the length of the endoscope. Preferably, the biopsy device 10 is made of a polymer or other biocompatible material and is secured to the distal end of the endoscope 12 with a friction fit.

The biopsy device 10 includes a number of chambers 14A, 14B, 14C . . . 14E disposed about its periphery. Each chamber has an opening that is oriented in the direction of the distal end of the endoscope for receiving tissue samples. Each of the chambers is isolated from the other chambers such that a tissue sample received in any single chamber does not commingle or interact with tissue samples received in any other chamber.

To obtain a tissue sample in the biopsy device, tissue is drawn into an individual chamber with a vacuum source or the like. A knife or cutter is passed over the opening of the chamber in order to cut the sample from a portion of the body and maintain it in place in the chamber.

In one embodiment of the invention, a rotating cap 20 moves a knife in front of each of the openings of the chambers to cut the tissue samples from the body. The cap 20 has an opening 22 that, when positioned in front of the a tissue chamber, allows tissue to enter the chamber. The biopsy device 10 has an annular ring 18 that surrounds the chambers 14A-14E and extends distally therefrom. The annular ring 18 forms a recess into which the rotating cap 20 is seated. Disposed across a portion of the opening 22 on the rotating cap 20 is a blade 24. When the cap 20 is rotated, tissue protruding through the opening 22 and into one of the biopsy chambers 14A-14E will be cut when the blade 24 is moved across the opening of the chamber.

In one embodiment of the invention, the cap 20 is rotated by an actuating thread 30 that winds around the perimeter of the cap in a groove or race 34 that is formed on the outer edge of the cap 20. In one embodiment of the invention, the actuating thread 30 forms a closed loop a portion of which extends to the proximal end of the endoscope 12. In one embodiment, the activating thread 30 extends through a catheter 36 that is positioned along the outside of the endoscope. Alternatively, the activating thread can be routed through an interior lumen of the endoscope 12. Under the control of a physician, the actuating thread is advanced such that the cap 20 is rotated within the area defined by the annular ring 18 and therefore around the openings of the biopsy chambers.

To maintain the rotating cap 20 in its seated position, a cover 50 having a number of openings 52A, 52B . . . 52E is placed over the rotating cap 20 and the annular ring 18. Each of the openings 52A-52E is aligned with the opening of a biopsy chamber 14A-14E.

Figure 2:
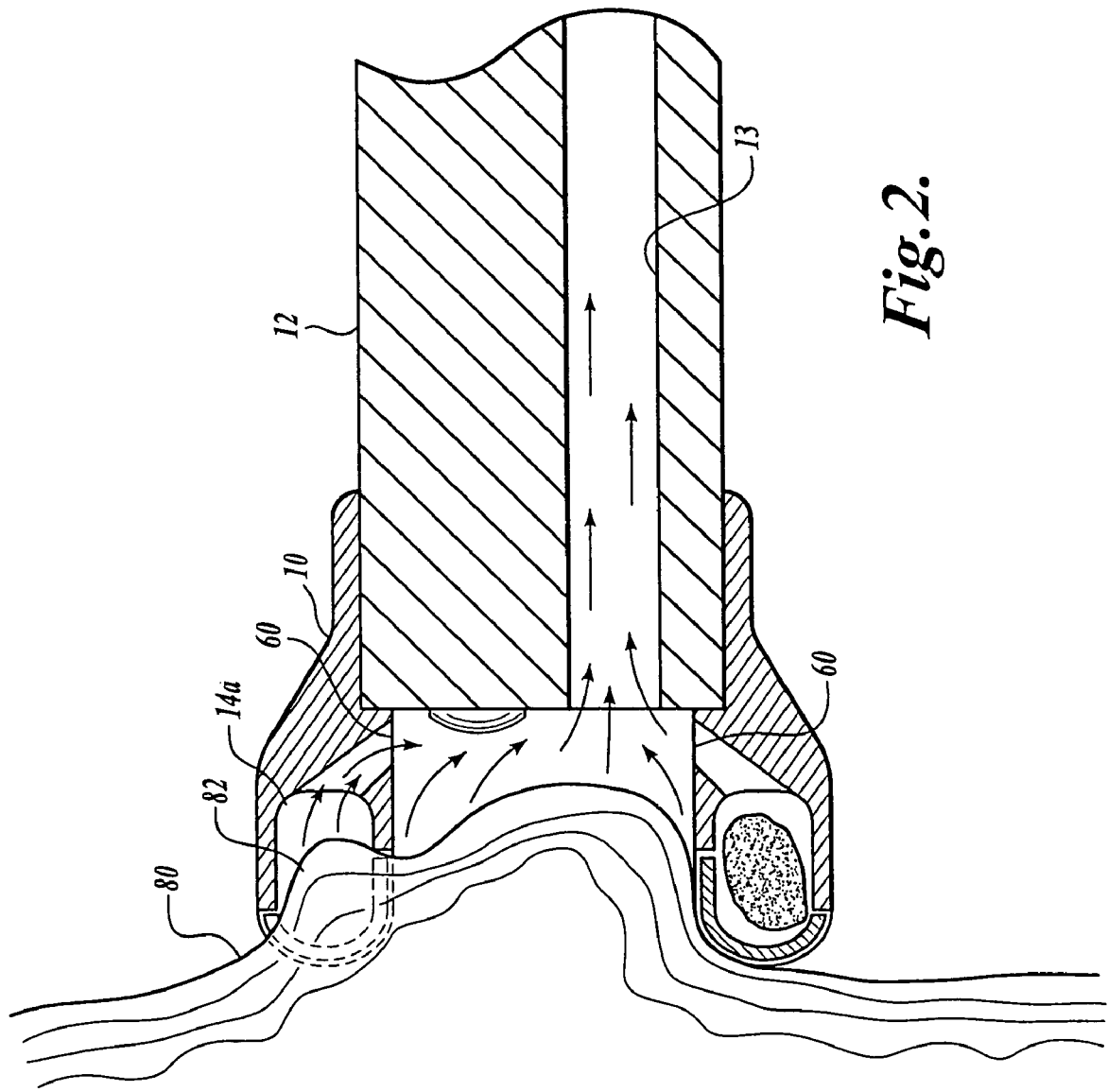
FIG. 2 illustrates how tissue is drawn into a biopsy chamber with a vacuum in accordance with one embodiment of the invention.

To draw tissue into the biopsy chambers, each chamber has one or more holes 60 that are in communication with a vacuum lumen 13 of the endoscope 12. As shown in FIG. 2, vacuum is applied from a location outside the body to the vacuum lumen 13 of the endoscope 12. The vacuum pressure is conveyed to the biopsy chambers 14A-14D through the one or more holes 60.

In the currently preferred embodiment of the invention, all biopsy chambers are covered with the exception of the chamber that is aligned with the opening 22 in the rotating cap 20. Therefore, tissue 80 is drawn into the chamber that is aligned with the opening 22 in the rotating cap 20. The blade 24 is moved with respect to the biopsy chamber thereby cutting the tissue 82 suctioned into the chamber and sealing the chamber with the rear surface of the rotating cap as the opening 22 in the cap 20 is rotated past the chamber.

Once the tissue sample has been captured in the chamber, the hole 22 in the rotating cap 20 is advanced so that it aligns with the opening of another chamber in order to obtain another tissue sample.

Once the physician has obtained as many biopsy samples as desired, the endoscope can be withdrawn from the body and the biopsy device 10 removed from the distal end of the endoscope. Each of the biopsy chambers 14A-14E is preferably marked or coded so that the tissue samples can be traced to a particular location in a patient's body.

Although the presently preferred embodiment of the invention uses an actuating thread to rotate the cap 20 with respect to each individual biopsy chamber, it will be appreciated that other mechanisms such as a pneumatic or hydraulic actuator could be used to rotate the cap 20. Alternatively, the rotating cap 20 could be moved with piezoelectric or other type of motor or with ratcheting mechanisms. Alternatively, chambers could be made movable in the biopsy device such that the blade 24 remains stationary and the biopsy chambers moved underneath the blade in order to achieve the relative movement of the biopsy chambers against the blade in order to remove a tissue sample from the body.

While the preferred embodiment of the invention has been illustrated and described, it will be appreciated that various changes can be made therein without departing from the scope of the invention. For example, the blade 24 could be an electrosurgical device or laser. Similarly the biopsy device 10 may have more than one cutting device to remove more than one tissue sample at a time from a particular location in the patient's body. It is therefore intended that the scope of the invention be determined from the following claims and equivalents thereto.

The embodiments of the invention in which an exclusive property or privilege is claimed are defined as follows:

1. A device for obtaining multiple biopsy samples from a patient, comprising:
   a cap including a step to engage the distal end face of an endoscope, the cap having first and second isolated biopsy chambers formed therein, each isolated biopsy chamber having an opening through which tissue can enter the biopsy chamber;
   a tissue cutter associated with the cap such that relative movement between the cutter and the first biopsy chamber and subsequent relative movement between the cutter and the second biopsy chamber sequentially cuts tissue that has entered the first and second biopsy chambers.

2. The device of claim 1, wherein each biopsy chamber includes a port in fluid communication with a vacuum lumen of the endoscope such that when vacuum is applied to the vacuum lumen, tissue is drawn into the first and/or second biopsy chamber.

3. The device of claim 1, wherein each of the biopsy chambers is marked with a code or other identification.

4. The device of claim 1, wherein the biopsy chambers substantially face the same direction as the distal end face of the associated endoscope.

5. The device of claim 1, further comprising means for creating relative movement between the cutter and the first biopsy chamber and subsequent relative movement between the cutter and the second biopsy chamber.

6. The device of claim 5, wherein the means for creating relative movement comprises an actuating thread that moves the cutter relative to the openings of the biopsy chambers.

7. The device of claim 6, wherein the cutter is mounted on a rotating ring that is moved by the actuating thread over the openings of the biopsy chambers.

8. The device of claim 5, wherein the means for creating relative movement moves the chambers with respect to the cutter.

9. The device of claim 5, further comprising a seal for closing the first biopsy chamber once a tissue sample is cut and received therein.

10. The device of claim 9, wherein the seal closes the first biopsy chamber and subsequently opens the second biopsy chamber for subsequent tissue collection.

11. The device of claim 9, wherein the seal and the cutter are integrally formed.

12. The device of claim 1, further comprising an actuator that causes, under control of the user, relative movement between the cutter and the first and second biopsy chambers.

13. The device of claim 1, wherein the first and second biopsy chambers are configured to contain the tissue cut by the tissue cutter until subsequent removal of the device from the patient.

14. The device of claim 13, wherein the first and second biopsy chambers each include a port in fluid communication with a vacuum lumen of the endoscope such that when vacuum is applied to the vacuum lumen, tissue is drawn into the first and/or second biopsy chamber.

15. The device of claim 1, wherein the cap includes a central lumen with at least two different radii.

16. The device of claim 15, wherein the central lumen of the cap has a proximal portion with a first radius configured to mate with the outer diameter of the endoscope.

17. The device of claim 16, wherein the central lumen of the cap has a distal portion with a second radius, the second radius being smaller than the first radius.

18. The device of claim 15, wherein the at least two radii for the step that is configured to engage the distal end face of the endoscope.

19. The device of claim 1, wherein the cap abuts the distal end face of the endoscope.

20. A medical system for obtaining multiple biopsy samples from a patient, comprising:
   an endoscope having a proximal end and a distal end;
   a biopsy device configured to be removably secured to the distal end face of the endoscope, the biopsy device comprising:
   a throughbore configured for interfacing with the distal end of the endoscope;
   a plurality of biopsy chambers arranged around and outwardly of the throughbore, each of the biopsy chambers having an opening in which tissue can be received, wherein the openings of the biopsy chambers face outwardly of the distal end face of the endoscope;
   a cutter for cutting tissue that enters the biopsy chambers;
   an actuator that moves the cutter under control of the user in a sequential manner between the plurality of biopsy chambers; and a seal for closing a biopsy chamber once tissue has been cut and received in the biopsy chamber.

21. The system of claim 20, wherein the biopsy device further comprises a rotatable ring having an opening that when positioned in front of the openings of the biopsy chambers allows tissue to enter the biopsy chambers, the cutter being fixedly attached to the ring adjacent the ring opening.

22. The system of claim 21, wherein the actuator imparts rotation on the ring.

23. The system of claim 20, wherein the plurality of chambers substantially face the same direction as the distal end face of the endoscope.

24. A method of obtaining multiple biopsy samples from a patient, comprising:
  inserting an endoscope into a patient having a cap secured to a distal end face of the endoscope, the cap including two or more biopsy chambers which face outwardly of the distal end face of the endoscope;
  obtaining a first tissue sample in a first biopsy chamber by applying vacuum to a first biopsy chamber to draw tissue into the first biopsy chamber;
  moving the first biopsy chamber relative to a tissue cutter to cut the tissue from the patient;
  sealing the first biopsy chamber; thereafter obtaining a second tissue sample in a second biopsy chamber;
  thereafter removing the endoscope from the patient; and
  removing the tissue samples from the first and/or second biopsy chamber.

25. The method of claim 24, wherein the act of moving the first biopsy chamber relative to a tissue cutter comprises one of a group consisting of:
  (a) rotating the tissue cutter relative to the first biopsy chamber; and
  (b) rotating the first biopsy chamber relative to the tissue cutter.

26. The method of claim 24, wherein obtaining a tissue sample in a second chamber includes
  moving the endoscope to a location within the patient different than the position where the first tissue sample was obtained;
  applying vacuum to the second chamber to draw tissue into the second biopsy chamber;
  moving, under control of the user, the second chamber relative to the tissue cutter to cut tissue from the patient; and
  sealing the second chamber.

* * * * *